United States Patent
Johnson

(10) Patent No.: US 12,359,261 B2
(45) Date of Patent: Jul. 15, 2025

(54) **ASSAY FOR DETECTION OF PATHOGENIC *LEPTOSPIRA* STRAINS**

(71) Applicant: Quest Diagnostics Investments LLC, Secaucus, NJ (US)

(72) Inventor: Erik P. Johnson, Carlsbad, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 556 days.

(21) Appl. No.: 17/154,781

(22) Filed: Jan. 21, 2021

(65) Prior Publication Data

US 2021/0164022 A1    Jun. 3, 2021

Related U.S. Application Data

(62) Division of application No. 15/563,037, filed as application No. PCT/US2016/025817 on Apr. 4, 2016, now Pat. No. 10,907,218.

(60) Provisional application No. 62/142,723, filed on Apr. 3, 2015.

(51) Int. Cl.
    *C12Q 1/68*      (2018.01)
    *C07H 21/04*     (2006.01)
    *C12Q 1/689*     (2018.01)

(52) U.S. Cl.
    CPC ............. *C12Q 1/689* (2013.01); *C07H 21/04* (2013.01); *Y02A 50/30* (2018.01)

(58) Field of Classification Search
    None
    See application file for complete search history.

(56) References Cited

U.S. PATENT DOCUMENTS

| 5,541,308 A | 7/1996 | Hogan et al. |
| 2009/0117557 A1 | 5/2009 | Wang et al. |
| 2014/0328803 A1 | 11/2014 | McKenzie et al. |

FOREIGN PATENT DOCUMENTS

| WO | WO-2014/197607 A1 | 12/2014 |
| WO | WO-2014/197607 A3 | 12/2014 |

OTHER PUBLICATIONS

Biotechniques (1999) 27(3):528-536.*
Xu et al; PLOS One, vol. 9, 2014.*
Fearnley et al., "The development of a real-time PCR to detect pathogenic *Leptospira* species in kidney tissue," Research in Veterinary Science, Aug. 1, 2008, 85(1):8-16.
Morey et al., "Species-Specific Identification of Leptospiraceae by 16S rRNA Gene Sequencing," Journal of Clinical Microbiology, Oct. 1, 2006, 44(10):3510-3516.
Slack et al., "Identification of pathogenic *Leptospira* species by conventional or real-time PCR and sequencing of the DNA gyrase subunit B encoding gene," BMC Microbiology, Oct. 27, 2006, 6(1):95, 1-10.
Supplementary European Search Report dated Nov. 2, 2018, in EP 16774393.9.
Tansuphasiri et al., "Development of a duplex-polymerase chain reaction for rapid detection of pathogenic leptospira," Southeast Asian Journal of Tropical Medicine and Public Health, Mar. 28, 2006, 37(2):297-308.
Villumsen et al., "Novel TaqMan® PCR for detection of *Leptospira* species in urine and blood: Pit-falls of in silico validation," Journal of Microbiological Methods, Jun. 29, 2012, 91(1):184-190.
Waggoner et al., "Sensitive Real-Time PCR Detection of Pathogenic *Leptospira* spp. and a Comparison of Nucleic Acid Amplification Methods for the Diagnosis of Leptospirosis," PLOS One, Nov. 7, 2014, 9(11):e112356. 1-8.
Bedir, Orhan et al., "Simultaneous Detection and Differentiation of Pathogenic and Nonpathogenic *Leptospira* spp. by Multiplex Real-Time PCT (TaqMan) assay," Polish Journal of Microbiology, 2010, vol. 59, No. 3, pp. 167-173.
Buck et al., "Design Strategies and Performance of Custom DNA Sequencing Primers," BioTechniques, Sep. 1999, vol. 27, No. 3, pp. 528-536.
International Preliminary Report of Patentability issued in application No. PCT/US2016/025817 on Oct. 6, 2017.
International Search Report issued in application No. PCT/US2016/025817 on Oct. 4, 2016.
Li, Chunjuan, "A TaqMan Fluorescent Quantitative Polymerase Chain Reaction assay for pathogenic *Leptospira* spp.", China Excellent Master's Thesis Full-text Database, Medical Science and Technology Series, 2012, No. 01, pp. E060-E087, published on Jan. 15, 2011.
Office Action and Search Report dated Sep. 27, 2020 in CN 201680032326.X, with English translation.
Smythe et al., "A quantitative PCR (TaqMan) assay for pathogenic *Leptospira* spp," BMC Infectious Diseases, Jul. 2002, vol. 2(13): 1-7.
Xu et al., PLOS One, Feb. 2014, vol. 9.

* cited by examiner

*Primary Examiner* — Jehanne S Sitton
(74) *Attorney, Agent, or Firm* — Foley & Lardner LLP

(57) ABSTRACT

The present invention provides methods and compositions for determining the presence and/or amount of pathogenic *Leptospira* in a test sample. In particular, substantially purified oligonucleotide primers and probes are described that can be used for qualitatively and quantitatively detecting pathogenic *Leptospira* nucleic acid in a test sample by amplification methods. The present invention also provides primers and probes for generating and detecting control nucleic acid sequences that provide a convenient method for assessing internal quality control of the *Leptospira* assay.

5 Claims, 2 Drawing Sheets
Specification includes a Sequence Listing.

ASSAY FOR DETECTION OF PATHOGENIC *LEPTOSPIRA* STRAINS

CROSS-REFERENCE TO RELATED APPLICATIONS

This application is a Divisional of U.S. application Ser. No. 15/563,037, which is the U.S. National Stage of PCT/US2016/025817, filed Apr. 4, 2016, which claims priority from U.S. Provisional Application No. 62/142,723, filed Apr. 3, 2015.

SEQUENCE LISTING

The instant application contains a Sequence Listing which has been submitted electronically in ASCII format and is hereby incorporated by reference in its entirety. Said ASCII copy, created on Jan. 15, 2021, is named sequence.txt and is 9,333 bytes in size.

FIELD OF THE INVENTION

The present invention relates generally to compositions and methods for detecting pathogenic *Leptospira* in a test sample.

BACKGROUND OF THE INVENTION

The following discussion of the background of the invention is merely provided to aid the reader in understanding the invention and is not admitted to describe or constitute prior art to the present invention.

Leptospirosis is caused by a waterborne spirochete of the genus *Leptospira*. Until recently, *Leptospira* species were grouped by serological data into two species, *Leptospira interrogans* and the non-pathogenic *L. biflexa*, together encompassing over 230 serovars. More recently, sequence information has allowed *Leptospira* to be grouped into 16 genomospecies, including *L. interrogans, biflexa, kirshneri, and borgpetersenii*. Unfortunately, the species cannot be neatly categorized into pathogenic and non-pathogenic, since both kinds of serovars are present in any given genomospecies. Despite this complication, *L. interrogans* serovars *icterohaemorrhagiae, copenhageni, lai, australis, and autumnalis* are among those most commonly found in humans, with *icterohaemorrhagiae* usually causing the most severe symptoms.

The source of *Leptospira* infection is through exposure to the urine of an infected animal, although direct contact is not necessary. Infection is often discovered in patients who have been in contact with contaminated bodies of water. *Leptospira* enters the body via cuts and abrasions or by contact with mucosa, incubation lasting from 2-20 days. The bacterium infects first the blood and then CSF, usually being cleared from both by the third week after symptoms present. *Leptospira* can be found in the urine within one week of symptom onset, and may continue to be present for months or years without treatment.

The symptoms of leptospirosis have a broad range of severity. Most infected individuals are asymptomatic or have very mild symptoms, and do not seek medical attention. Some, however have more severe symptoms which can lead to death. Symptoms can arise suddenly and include fever, chills, headache, body aches, abdominal pain, conjunctival suffusion, and sometimes a skin rash. The headaches and myalgia may be severe, and up to 25% of patients suffer from aseptic meningitis. Between 5 and 10% of all leptospirosis patients have icteric leptospirosis, sometimes called Weil's disease, which is a more severe condition that is fatal in 5 to 15% of cases. Symptoms include those in the anicteric disease and may also include jaundice, liver failure or acute renal failure in many cases. Respiratory and cardiac involvement is also common and can lead to respiratory distress syndrome or myocarditis.

The detection of *Leptospira* in the clinical setting is cumbersome. Serological studies are time consuming and complex, and culture can take from 6 to 26 weeks. In addition, the bacterium quickly loses viability in urine, the primary sample type, and culture tests provide limited utility. In contrast, real-time PCR detection is fast, sensitive, and does not require organism viability. Samples can be frozen or mixed with preservative for transport. While the taxonomy of *Leptospira* is complex, 16S sequence data suggests that pathogenic and non-pathogenic subspecies may be distinguished by PCR. The disclosed methods and compositions are designed to detect pathogenic species only. Non-pathogenic species like *L. biflexa* are not detected. In addition, utilizing PCR-based methods will allow testing of blood, CSF, or urine to give an indication of the stage of infection when tested early.

Several reports disclose assays of patient samples following a nucleic acid amplification step, such as PCR (Brown et al., Evaluation of the polymerase chain reaction for early diagnosis of leptospirosis. J. Med. Microbiol. 43:110-114, 1995 and Smythe et al., A quantitative PCR (TaqMan) assay for pathogenic *Leptospira* spp. BMC Infectious Diseases. 2(13), 2002), but these references do not teaches a method of detecting only pathogenic *Leptospira* DNA. Other relevant references describe the current understanding of the genotypic differences in *Leptospira* serovars (Levett, P. N., Leptospirosis. Clinical Microbiology Reviews. 14(2):296-36, 2001; Brenner et al., Further determination of DNA relatedness between serogroups and serovars in the family Leptospiraceae with a proposal for *Leptospira alexanderi* sp. nov. and four new *Leptospira* genomospecies. Int. J. Syst. Bacteriol. 49:839-858, 1999; Ramadass et al., Genetic characterization of pathogenic *Leptospira* species by DNA hybridization. Int. J. Syst. Bacteriol. 42:215-219, 1992; Yasuda et al., Deoxyribonucleic acid relatedness between serogroups and serovars in the family Leptospiraceae with proposals for seven new *Leptospira* species. Int. J. Syst. Bacteriol. 37:407-415, 1987; World Health Organization. Leptospirosis worldwide, 1999. Wkly. Epidemiol. Rec. WHO 75:217-223, 1999; Edwards and Domm, Human leptospirosis. Medicine 39:117-156, 1960; Kelly, Leptospirosis. p. 1580-1587 from: Gorbach, S. L. et al., Infectious Diseases, 2nd Edition, W.B. Saunders, Philadelphia PA, 1998).

Yet, in spite of the knowledge in the art, there is not currently a method for detecting only pathogenic serovars of *Leptospira* or an assay that is also capable of distinguishing pathogenic *Leptospira* from other spirochetes. The compositions and methods disclosed herein are intended to provide such a method.

SUMMARY OF THE INVENTION

The present invention provides methods and compositions for determining the presence and/or amount of pathogenic *Leptospira* nucleic acids in a test sample. In particular, the invention provides substantially purified oligonucleotides for qualitatively and quantitatively detecting *Leptospira* nucleic acids in a test sample and amplification methods are described herein. The present invention can provide a specific, sensitive method that exhibits a broad dynamic range of detection of pathogenic *Leptospira* without detecting unrelated spirochetes or non-pathogenic serovars, and which can advantageously provide quantitative as well as qualitative results. The invention may be used alone, or in combination with clinical symptoms or other indicators, for diagnosing an individual as having pathogenic *Leptospira*.

Accordingly, in one aspect, the disclosure provides oligonucleotide primers and probes used in the methods described herein to provide an assay for detecting pathogenic *Leptospira*. In certain embodiments, the invention provides a substantially purified oligonucleotide having a sequence selected from the group consisting of:

```
                                            (SEQ ID NO: 1)
5'-AGTAACACGTGGGTAATCTTCCT-3', (SEQ ID NO: 2)
5'-TCTCTCGGGACCATCCAGTA-3',
and (SEQ ID NO: 3)
5'-TGGGATAACTTTCCGAAAGGGAAG C-3',
``` wherein the oligonuclotide is attached either directly or indirectly to a detectable label.

Direct or indirect attachment can mean that the label can be incorporated into, associated with or conjugated to the oligonucleotide, or the attachment may comprise a spacer arm of various lengths. Attachment may be by covalent or non-covalent means as long as the oligonucleotide is detectable by the means disclosed herein and known in the art.

The detectable label may be a fluorescent dye or the detectable label may comprise a reporter dye and a quencher. In some embodiments, the oligonucleotide of the invention may be

```
                                            (SEQ ID NO: 3)
5' [6~FAM]-TGGGATAACTTTCCGAAAGGGAAGC -[BHQ-1] 3'.
```

In some embodiments, the invention provides a pair of substantially pure oligonucleotide primers comprising SEQ ID NO: 1 and SEQ ID NO: 2. The primers may be detectably labeled and they may be used in conjunction with a detectably labeled probe. The primer pair can be suitable for amplifying the 16S gene of pathogenic *Leptospira* or a fragment or complement thereof including, but not limited to, SEQ ID NO: 4. The 16S gene sequences of numerous pathogenic *Leptospira* serovars are known in that art, and in some embodiments, the invention provides for primer pairs that are suitable for amplifying the 16S gene sequences of pathogenic *Leptospira* serovars, but which do not comprise SEQ ID NO: 1 or 2.

In one aspect, the invention provides a detection method for identifying the presence or absence of pathogenic *Leptospira* in a test sample, comprising detecting the presence or absence of a 16S target nucleic acid comprising at least 15 contiguous nucleotides that are at least 95% identical to SEQ ID NO: 4, SEQ ID NO: 5, SEQ ID NO: 6, SEQ ID NO: 11, SEQ ID NO: 12, SEQ ID NO: 13, or a fragment or complement thereof, wherein the presence of said 16S target nucleic acid identifies the presence of pathogenic *Leptospira*.

In some embodiments, the detection method further comprises: (a) providing a primer pair suitable for amplifying the 16S target nucleic acid or a fragment thereof, and providing a detectably labeled probe suitable for hybridizing to the 16S target nucleic acid or a fragment thereof, (b) performing a primer extension reaction comprising the primer pair of step (a) under conditions suitable to produce a first reaction product when the 16S target nucleic acid is present in said sample, and (c) determining the presence or absence of pathogenic *Leptospira* by detecting the presence or absence of the detectable label of the probe.

In another aspect, the invention provides that at least one member of the primer pair used in the detection method comprises SEQ ID NO: 1 or SEQ ID NO: 2. Alternatively, at least one member of the primer pair consists of SEQ ID NO: 1 or SEQ ID NO: 2. In another aspect, the detectably labeled probe may comprise SEQ ID NO: 3 or consist of 5' [6~FAM]-TGGGATAACTTTCCGAAAGGGAAGC-[BHQ-1] 3' (SEQ ID NO: 3).

In one aspect, the invention provides a method for detecting the presence or amount of pathogenic *Leptospira* nucleic acids in a test sample, comprising:
  (a) amplifying pathogenic *Leptospira* nucleic acids if present in the sample using a pair of oligonucleotide primers having the sequences set forth in SEQ ID NO: 1 and SEQ ID NO: 2;
  (b) hybridizing said amplified pathogenic *Leptospira* nucleic acids with an oligonucleotide probe having the sequence set forth in SEQ ID NO: 3 in the presence of an enzyme that cleaves said probe when said probe hybridizes to said pathogenic *Leptospira* nucleic acids; and
  (c) detecting a signal from said probe, wherein said signal indicates the presence or amount of pathogenic *Leptospira* nucleic acids in said test sample.

In some embodiments, the test sample can be selected from the group consisting of serum, blood, plasma, cerebral spinal fluid, synovial fluid, and urine. In some embodiments, the pathogenic *Leptospira* nucleic acids are extracted from the test sample prior to amplifying the nucleic acids, while in other embodiments, the test sample may be used directly. In some embodiments, the probe may comprise a reporter dye and a quencher, and in some embodiments, the reporter dye can be 6~FAM and the quencher can be BHQ-1.

In one aspect, the invention provides a method of diagnosing an individual suspected of having pathogenic *Leptospira*, comprising:
  (a) obtaining a sample from said individual suspected of having pathogenic *Leptospira*,
  (b) extracting substantially pure nucleic acids from the sample,
  (c) performing an amplification reaction in the presence of a detectably labeled probe comprising SEQ ID NO: 3 and a primer pair comprising SEQ ID NO: 1 and SEQ ID NO: 2, wherein hybridization of the detectably labeled probe to a corresponding sequence of the nucleic acids from the sample in the presence of a polymerizing enzyme will cleave the detectable label from the probe when the nucleic acids from the sample are amplified by the primer pair,
  (d) detecting a signal from the detectable label of the probe, wherein said signal indicates the presence or amount of pathogenic *Leptospira* nucleic acids in the sample, and
  (e) determining that the individual suspected of having pathogenic *Leptospira* has pathogenic *Leptospira* if the signal is detected or diagnosing the individual as not having pathogenic *Leptospira* if the signal is not detected.

In some embodiments, the amplification reaction may comprise real-time PCR. In some embodiments, the probe may comprise a reporter dye and a quencher, and in some embodiments, the reporter dye can be 6~FAM and the quencher can be BHQ-1.

In one aspect, the invention provides a kit comprising a primer pair that specifically hybridize to a target nucleic comprising SEQ ID NO: 4, a fragment, or a complement thereof, and a probe that specifically hybridizes the target nucleic acid of SEQ ID NO: 4, a fragment, or a complement thereof.

In some embodiments of the kit, at least one member of the primer pair comprises the sequence of SEQ ID NO: 1 or 2, or a complement thereof. In some embodiments, the primer pairs consists a first primer and a second primer, wherein the first primer comprises SEQ ID NO: 1, or a complement thereof, and the second primer comprises SEQ ID NO: 2, or a complement thereof. In some embodiments, the probe may comprise SEQ ID NO: 3, or a complement thereof. In some embodiments, the detectable label on the probe comprises a reporter dye and a quencher, and in some embodiments, the reporter dye can be 6~FAM and the quencher can be BHQ-1.

In another aspect, the invention provides a kit comprising a primer pair that specifically hybridize to a target nucleic acid comprising SEQ ID NO: 5, SEQ ID NO: 6, SEQ ID NO: 12, SEQ ID NO: 13, or a fragment or complement thereof, and a detectably labeled probe that specifically hybridizes to the target nucleic acid comprising SEQ ID NO: 5, SEQ ID NO: 6, SEQ ID NO: 12, SEQ ID NO: 13, or a fragment, or a complement thereof. In some embodiments, the detectable label comprises a reporter dye and a quencher, and in some embodiments, the reporter dye can be 6~FAM and the quencher can be BHQ-1.

BRIEF DESCRIPTION OF FIGURES

FIG. 1A shows high positive, low positive, and negative results in a linear view. FIG. 1B shows high positive, low positive, and negative results in a log view.

DETAILED DESCRIPTION OF THE INVENTION

Figure 1A:
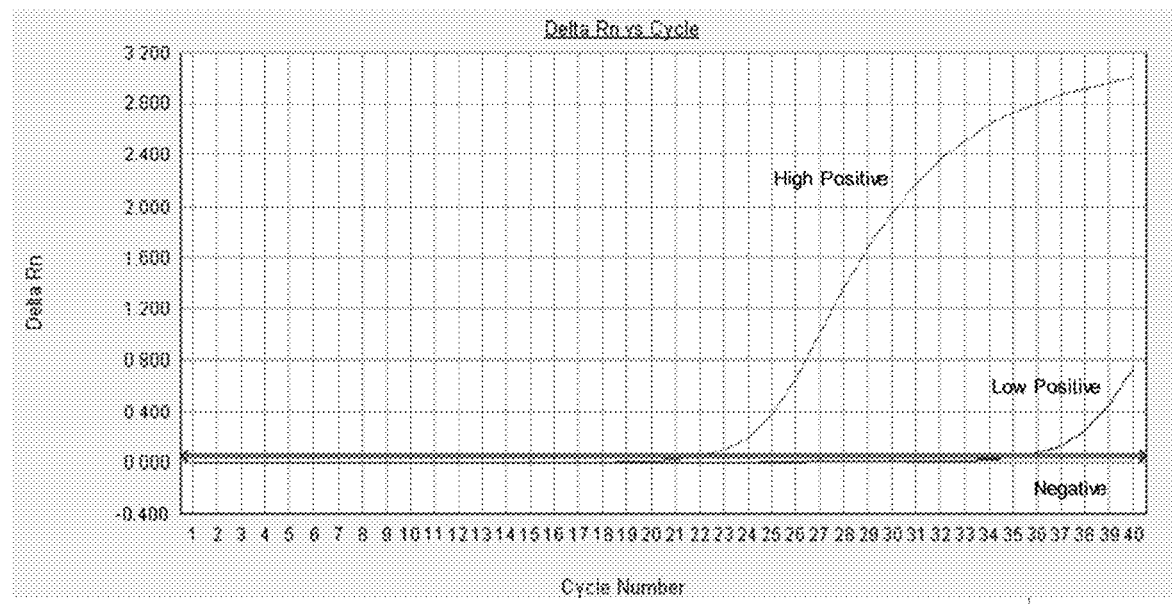
FIGS. 1A-1B show typical amplification plots from the disclosed *Leptospira* assay.

The present invention provides methods and compositions for the rapid and sensitive determination of pathogenic *Leptospira* nucleic acids in test samples. In particular, oligonucleotide probes and primers are described that can be used in methods for quantitatively or qualitatively detecting pathogenic *Leptospira* nucleic acids in a sample. The present invention also provides primers and probes for generating and detecting control nucleic acid sequences that provide a convenient method for assessing internal quality control of the disclosed *Leptospira* assay.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, "about" means plus or minus 10%.

As used herein, the term "substantially purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion, extraction or isolation from a sample, or PCR. A "substantially purified" oligonucleotide is preferably greater than 50% pure, more preferably at least 75% pure, and even more preferably at least 95% pure, and most preferably 98% pure.

As used herein, the term "oligonucleotides" refers to a short polymer composed of deoxyribonucleotides, ribonucleotides or any combination thereof. These oligonucleotides are at least 5 nucleotides in length, preferably 10 to 70 nucleotides long, with 15 to 26 nucleotides being the most common. In certain embodiments, the oligonucleotides are joined together with or linked to a detectable label.

Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

As used herein, the term "suitable for amplifying," when referring to oligonucleotide primer or primer pairs, is meant primers that specifically hybridize to a target nucleic acid and are capable of providing an initiation site for a primer extension reaction in which a complementary copy of the target nucleic acid is synthesized.

As used herein, the term "hybridize" refers to process that two complementary nucleic acid strands anneal to each other under appropriately stringent conditions. Hybridizations are typically and preferably conducted with probe-length nucleic acid molecules, preferably 10-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, NY. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, NY; Ausubel, F. M. et al. 1994, Current Protocols in Molecular Biology. John Wiley & Sons, Secaucus, N.J.

The term "stringent hybridization conditions" as used herein refers to hybridization conditions at least as stringent as the following: hybridization in 50% formamide, 5×SSC, 50 mM NaH2PO4, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The terms "target nucleic acid" or "target sequence" as used herein refer to a sequence which includes a segment of nucleotides of interest to be amplified and/or detected. Copies of the target sequence which are generated during the amplification reaction are referred to as amplification products or amplicons. Target nucleic acids may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom, or may include extracted nucleic acids further converted using a bisulfite reaction.

As used herein, the term "*Leptospira* nucleic acids" refers to DNA and/or RNA comprising a contiguous sequence from a *Leptospira* genome, or the complement thereof. *Leptospira* nucleic acids may be *Leptospira* genomic DNA, *Leptospira* messenger RNA, or the complement of these sources, obtained by any method including obtaining the nucleic acid from a biological source, synthesizing the nucleic acid in vitro, or amplifying the nucleic acid by any method known in the art.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplicon" or "amplification product." While the exemplary methods described hereinafter generally relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, CA 1990, pp 13-20; Wharam, et al., Nucleic Acids Res. 2001 Jun. 1; 29(11):E54-E54; Hafner, et al., Biotechniques 2001 April; 30(4):852-6, 858, 860; Zhong, et al., Biotechniques 2001 April; 30(4):852-6, 858, 860.

The term "complement" "complementary" or "complementarity" as used herein with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-S'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA. The term "substantially complementary" as used herein means that two sequences specifically hybridize (defined above). The skilled artisan will understand that substantially complementary sequences need not hybridize along their entire length.

As used herein, the term "sample," "test sample," or "biological sample" refers to any liquid or solid material believed to comprise *Leptospira* nucleic acids. In preferred embodiments, a test sample is obtained from a biological source, such as cells in culture or a tissue or fluid sample from an animal, most preferably, a human. Preferred samples of the invention include, but are not limited to, plasma, serum, whole blood, blood cells, lymphatic fluid, cerebrospinal fluid, synovial fluid, urine, saliva, and skin or other organs (e.g. biopsy material). The term "patient sample" as used herein may also refer to a tissue sample obtained from a human seeking diagnosis or treatment of a disease related to a *Leptospira* infection. Each of these terms may be used interchangeably.

The term "detectable label" as used herein refers to a composition or moiety that is detectable by spectroscopic, photochemical, biochemical, immunochemical, electromagnetic, radiochemical, or chemical means such as fluorescence, chemifluoresence, or chemiluminescence, or any other appropriate means. Preferred detectable labels are fluorescent dye molecules, or fluorochromes, such as fluorescein, phycoerythrin, CY3, CY5, allophycocyanine, Texas Red, peridenin chlorophyll, cyanine, FAM, 6~FAM, JOE, TAMRA, tandem conjugates such as phycoerythrin-CY5, and the like. These examples are not meant to be limiting.

The term "fluorochrome" as used herein refers to a molecule that absorbs a quantum of electromagnetic radiation at one wavelength, and emits one or more photons at a different, typically longer, wavelength in response. In preferred embodiments, a fluorochrome can be a member of a pair of physically linked fluorochromes that exhibit fluorescence energy transfer. An energy transfer pair may be excited by a quantum of electromagnetic radiation at a wavelength at which the donor fluorochrome is excited; however, fluorescence from the donor fluorochrome that would be expected in the absence of the acceptor is quenched at least in part, and emission at an emission wavelength of the acceptor fluorochrome is observed.

In particularly preferred embodiments, a fluorochrome is one member of a physically linked "molecular beacon" pair. In these embodiments, the molecular beacon pair may be excited by a quantum of electromagnetic radiation at a wavelength at which a first fluorochrome member of the pair is excited; however, fluorescence from the first fluorochrome that would be expected in the absence of the second fluorochrome is quenched at least in part. Unlike energy transfer pairs, however, emission at an emission wavelength of the acceptor fluorochrome is not observed. Thus, these labels comprise a pair of dyes, one of which is referred to as a "reporter," and the second of which is referred to as a "quencher." When the two dyes are held in close proximity, such as at the ends of a nucleic acid probe, the quencher moiety prevents detection of a fluorescent signal from the reporter moiety. When the two dyes are separated, however, the fluorescent signal from the reporter moiety becomes detectable.

As used herein, "Scorpion primer" or "Scorpion probe" refers to an oligonucleotide having a 3' primer with a 5' extended probe tail having a hairpin structure which possesses a fluorophore/quencher pair. Optionally, the Scorpion primer/probe further contains an amplification blocker (e.g., hexethylene glycol ("BEG") separating the probe moiety from the primer moiety.

As used herein, the term "Scorpion detection system" refers to a method for real-time PCR. This method utilizes a bi-functional molecule (referred to herein as a "Scorpion"), which contains a PCR primer element covalently linked by a polymerase-blocking group to a probe element. Additionally, each Scorpion molecule contains a fluorophore that interacts with a quencher to reduce the background fluorescence.

As used herein, the term "detecting" used in context of detecting a signal from a detectable label to indicate the presence of a target nucleic acid in the sample does not require the method to provide 100% sensitivity and/or 100% specificity. As is well known, "sensitivity" is the probability that a test is positive, given that the person has a target nucleic acid sequence, while "specificity" is the probability that a test is negative, given that the person does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

As used herein "TaqMan® PCR detection" refers to a method for real time PCR. In this method, a TaqMan® probe which hybridizes to the nucleic acid segment amplified is included in the PCR reaction mix. The TaqMan® probe comprises a reporter dye and a quencher fluorophore on either end of the probe and in close enough proximity to each other so that the fluorescence of the reporter is taken up by the quencher. However, when the probe hybridizes to the amplified segment, the 5'-exonuclease activity of the Taq polymerase cleaves the probe thereby allowing the reporter fluorophore to emit fluorescence which can be detected.

A "fragment" in the context of a gene fragment refers to a sequence of nucleotide residues which are at least about 20 nucleotides, at least about 25 nucleotides, at least about 30 nucleotides, at least about 40 nucleotides, at least about 50 nucleotides, or at least about 100 nucleotides. The fragment is typically less than about 400 nucleotides, less than about 300 nucleotides, less than about 250 nucleotides, less than about 200 nucleotides, or less than 150 nucleotides. In certain embodiments, the fragments can be used in various hybridization procedures or microarray procedures to identify specific pathogens.

By "isolated", when referring to a nucleic acid (e.g., an oligonucleotide) is meant a nucleic acid that is apart from a substantial portion of the genome in which it naturally occurs. For example, any nucleic acid that has been produced synthetically (e.g., by serial base condensation) is considered to be isolated. Likewise, nucleic acids that are recombinantly expressed, produced by a primer extension reaction (e.g., PCR), or otherwise excised from a genome are also considered to be isolated.

The term "linker" as used herein refers to one or more chemical bonds or a chemical group used to link one moiety to another, serving as a divalent bridge, where it provides a group between two other chemical moieties.

*Leptospira* Assay:

The compositions and methods disclosed herein comprise primers and probes for the amplification and detection of a target DNA sequence from *Leptospira*. The disclosed DNA primers hybridize to flanking target regions within the 16S ribosomal RNA gene of pathogenic strains of *Leptospira* such as *L. interrogans* and *L. kirchneri*. The DNA primers used in this assay do not hybridize to the 16S gene of non-pathogenic strains such as *L. biflexa*, or to strains of intermediate pathogenicity like *L. illini*. The disclosed compositions and methods will also allow detection of pathogenic strains only common in particular regions of the world, *L. santarosai*, and *L. weilii*.

In some embodiments, the methods comprise obtaining a biological sample from a subject, extracting DNA from the sample, and performing a detection assay on the extracted DNA in which the DNA is contacted with a detectably labeled probe and primers that are specific for the 16S ribosomal RNA gene of pathogenic strains of *Leptospira*.

Sample Collection and Preparation:

Samples may comprise blood, plasma, urine, saliva, cerebral spinal fluid (CSF), tissue samples, or other commonly utilized types of biological sample.

In some embodiments, urine may be collected in a sterile, plastic container with a leak-proof cap and then frozen at −20 to −70° C. Repeated freezing and thawing should be avoided. Urine samples may be transported frozen, or, alternatively, immediately transferred into a specific urine transport tube, such as an Aptima® Urine Specimen Transport Tube.

In some embodiments, CSF may be collected in a sterile, plastic container with a leak-proof cap. Alternatively, blood may be collected in sterile tubes, preferably containing EDTA or another anticoagulant. These samples may be stored and transported while refrigerated at 2-8° C.

Nucleic Acid Isolation or Extraction:

The nucleic acid (DNA or RNA) may be isolated from a sample according to any methods well known to those of skill in the art. If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acids derived from the pathogens, if present in the sample, to detect using polymerase chain reaction. DNA extraction methods may include, but are not limited to, ethanol precipitation, organic extraction such as phenol-chloroform extraction, salting out or salt precipitation, cesium chloride density gradients, anion-exchange methods, silica-based methods including commercially available column kits, and automated high-throughput purification systems.

In one embodiment, DNA extraction may be performed using a MagNA Pure LC automated nucleic acid extraction system or a similar automated nucleic acid extraction system. Numerous commercial kits also yield suitable DNA including, but not limited to, QIAamp™ mini blood kit, Agencourt Genfind™, Roche Cobas® Roche MagNA Pure® or phenol-chloroform extraction using Eppendorf Phase Lock Gels®.

*Leptospira* Specific Primers and Probes:

In various embodiments of the present invention, oligonucleotide primers and probes can be used in the methods described herein to amplify and detect target sequences of pathogenic *Leptospira*. In certain embodiments, target nucleic acids may include the 16S ribosomal RNA gene of pathogenic strains of *Leptospira* such as *L. interrogans* and *L. kirchneri*. In addition, a second set of primers can also be used to amplify one or more control nucleic acid sequences. The target nucleic acids described herein may be detected singly or in a multiplex format, utilizing individual labels for each target.

The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill in the art.

In a preferred embodiment, the *Leptospira* specific primers are 5'-AGTAACACGTGGGTAATCTTCCT-3' (SEQ ID NO: 1) and 5'-TCTCTCGGGACCATCCAGTA-3' (SEQ ID NO: 2), although the skilled artisan will understand that other probes may be used. Alternative primers may be 70, 75, 80, 85, 90, 95, 96, 97, 98, or 99% identical to SEQ ID NO: 1 or SEQ ID NO: 2. In other embodiments, primers may be designed such that they bind to and are suitable for amplifying a target sequence of the *Leptospira* 16S gene. For instance, primers may be designed to amplify SEQ ID NO: 4, SEQ ID NO: 5, SEQ ID NO: 6, SEQ ID NO: 11, SEQ ID NO: 12, SEQ ID NO: 13, or fragments or complements thereof.

Primers may be between 10 and 30 nucleotides long. For instance, primers may be 10, 11, 12, 13, 14, 15, 16, 17, 18, 19, 20, 21, 22, 23, 24, 25, 26, 27, 28, 29, or 30 nucleotides in length. One of skill in the art will understand that the precise length and composition of the primer is dependent on the sample and the assay conditions. As disclosed herein, SEQ ID NO: 4, SEQ ID NO: 5, SEQ ID NO: 6, SEQ ID NO: 11, SEQ ID NO: 12, SEQ ID NO: 13, or fragments or complements thereof provide suitable target sequences for designing primers capable of detecting pathogenic *Leptospira*. In some embodiments primers comprising 10-30 nucleotides of SEQ ID NO: 4, SEQ ID NO: 5, SEQ ID NO: 6, SEQ ID NO: 11, SEQ ID NO: 12, SEQ ID NO: 13, or fragments or complements thereof may be used for the detection of pathogenic *Leptospira*. In other embodiments, primers that are at least 90%, at least 95%, or at least 99% identical to sequences comprising 10-30 nucleotides of SEQ ID NO: 4, SEQ ID NO: 5, SEQ ID NO: 6, SEQ ID NO: 11, SEQ ID NO: 12, SEQ ID NO: 13, or fragments or complements thereof may be used for the detection of pathogenic *Leptospira*. SEQ ID NO: 4, SEQ ID NO: 5, SEQ ID NO: 6 SEQ ID NO: 11, SEQ ID NO: 12, and SEQ ID NO: 13 are shown in Table 1.

TABLE 1

16S Sequences

| SEQ ID NO | Sequence |
|---|---|
| 4 | 5'-AACTAACGCTGGCGGCGCGTCTTAAACATGCAAGTCAAGCGGAGTAGCAATACTCAG CGGCGAACGGGTGAGTAACACGTGGGTAATCTTCCTCCGAGTCTGGGATAACTTTCCGAA AGGGGAGCTAATACTGGATGGTCCCGAGAGAGGTCATATGATTTTTCGGGTAAAGATTTA TTGCTCGGAGCTGAGCCCGCGCCCGATTAGCTAGTTGGTGAGGTAATGGCTCACCAAGGC GACGATCGGTAGCCGGCCTGAGAGGGTGTTCGGCCACAATGGAACTGAGACACGGTCCA TACTCCTACGGGAGGCAGCAGTTAAGAATCTTGCTCAATGGGGGGAACCCTGAAGCAGC GACGCCGCGTGAACGATGAAGGTCTTCGGATTGTAAAGTTCAATAAGCAGGGAAAAATA AGCAGCGATGTGATGATGGTACCTGCCTAAAGCACCGGCTAACTACGTGCCAGCAGCCG CGGTAATACGTATGGTGCAAGCGTTGTTCGGAATCATTGGGCGTAAAGGGTGCGTAGGC GGACATGTAAGTCAGGTGTGAAAACTGCGGGCTCAACTCGCAGCCTGCACTTGAAACTA TGTGTCTGGAGTTTGGGAGAGGCAAGTGGAATTCCAGGTGTAGCGGTGAAATGCGTAGA TATCTGGAGGAACACCAGTGGCGAAGGCGACTTGCTGGCCTAAAACTGACGCTGAGGCA CGAAAGCGTGGGTAGTGAACGGGATTAGATACCCCGGTAATCCACGCCCTAAACGTTGT CTACCAGTTGTTGGGGGTTTTAACCCTCAGTAACGAACCTAACGGATTAAGTAGACCGCC TGGGGACTATGCTCGCAAGAGTGAAACTCAAAGGAATTGACGGGGGTCCGCACAAGCGG TGGAGCATGTGGTTTAATTCGATGATACGCGAAAAACCTCACCTAGGCTTGACATGGAGT GGAATTATGTAGAGATACATGAGCCTTCGGGCCGCTTCACAGGTGCTGCATGGTTGTCGT CAGCTCGTGTCGTGAGATGTTGGGTTAAGTCCCGCAACGAGCGCAACCCTCACCTTATGT TGCCATCATTTAGTTGGGCACTCGTAAGGAACTGCCGGTGACAAACCGGAGGAAGGCGG GGATGACGTCAAATCCTCATGGCCTTTATGTCTAGGGCAACACACGTGCTACAATGGCCG GTACAAAGGGTAGCCAACTCGCGAGGGGGAGCTAATCTCAAAAAGCCGGTCCCAGTTCG GATTGGAGTCTGCAACTCGACTCCATGAAGTCGGAATCGCTAGTAATCGCGGATCAGCAT GCCGCGGTGAATACGT-3' |
| 5 | 5'-AACTAACGCTGGCGGCGCGTCTTAAACATGCAAGTCAAGCGGAGTAGCAATACTCAG CGGCGAACGGGTGAGTAACACGTGGGTAATCTTCCTCCGAGTCTGGGATAACTTTCCGAA AGGGGAGCTAATACTGGATGGTCCCGAGAGAGGTCATATGATTTTTCGGGTAAAGATTTA TTGCTCGGAGCTGAG-3' |
| 6 | 5'-GTGTTCGGCCACAATGGAACTGAGACACGGTCCATACTCCTACGGGAGGCAGCAGTT AAGAATCTTGCTCAATGGGGGAACCCTGAAGCAGCGACGCCGCGTGAACGATGAAGGT CTTCGGATTGTAAAGTTCAATAAGCAGGGAAAAATAAGCAGCGATGTGATGATGGTACC TGCCTAAAGCACCGGCTAACTACGTGCCAGCAGCCGCGGTAATACGTATGGTGCAAGCG TTGTTCGGAATCATTGGGCGTAAAGGGTGCGTAGGCGGACATGTAAGTCAGGTGTGAAA ACTGCGGGCTCAACTCGCAGCCTGCACTTGAAACTATGTGTCTGGAGTTTGGGAGAGGCA AGTGGAATTCCAGGTGTAGCGGTGAAATGCGTAGATATCTGGAGGAACACCAGTGGCGA AGGCGACTTGCTGGCCTAAAACTGACGCTGAGGCACGAAAGCGTGGGTAGTGAACGGGA TTAGATACCCCGGTAATCCACGCCCTAAACGTTGTCTACCAGTTGTTGGGGGTTTTAACCC TCAGTAACGAACCTAACGGATTAAGTAGACCGCCTGGGGACTATGCTCGCAAGAGTGAAA CTCAAAGGAATTGACGGGGGTCCGCACAAGCGGTGGAGCATGTGGTTTAATTCGATGATA CGCGAAAAACCTCACCTAGGCTTGACATGGAGTGGAATTATGTAGAGATACATGAGCCTTC GGGCCGCTTCACAGGTGCTGCATGGTTGTCGTCAGCTCGTGTCGTGAGATGTTGGGTTAAG TCCCGCAACGAGCGCAACCCTCACCTTATGTTGCCATCATTTAGTTGGGCACTCGTAAGGA ACTGCCGGTGACAAACCGGAGGAAGGCGGGGATGACGTCAAATCCTCATGGCCTTTATGT CTAGGGCAACACACGTGCTACAATGGCCGGTACAAAGGGTAGCCAACTCGCGAGGGGGA GCTAATCTCAAAAAGCCGGTCCCAGTTCGGATTGGAGTCTGCAACTCGACTCCATGAAGT CGGAATCGCTAGTAATCGCGGATCAGCATGCCGCGGTGAATACGT-3' |

TABLE 1 -continued

16S Sequences

SEQ
ID
NO Sequence 11  5'-AACTAACGCTGGCGGCGCGTCTTAAACATGCAAGTCAAGCGGAGTAGCAATACTCA
    GCGGCGAACGGGTGAGTAACACGTGGGTAATCTTCCTCTGAGTCTGGGATAACTTTCCGA
    AAGGGAAGCTAATACTGGATGGTCCCGAGAGATCATAAGATTTTTCGGGTAAAGATTTATT
    GCTCGGAGATGAGCCCGCGTCCGATTAGCTAGTTGGTGAGGTAAAGGCTCACCAAGGCGA
    CGATCGGTAGCCGGCCTGAGAGGGTGTTCGGCCACAATGGAACTGAGACACGGTCCATAC
    TCCTACGGGAGGCAGCAGTTAAGAATCTTGCTCAATGGGGGGAACCCTGAAGCAGCGACG
    CCGCGTGAACGATGAAGGTCTTCGGATTGTAAAGTTCAGTAAGCAGGGAAAAATAAGCAG
    CAATGTGATGATGGTACCTGCCTAAAGCACCGGCTAACTACGTGCCAGCAGCCGCGGTAAT
    ACGTATGGTGCAAGCGTTGTTCGGAATCATTGGGCGTAAAGGGTGCGTAGGCGGACATGTA
    AGTCAGGTGTGAAAACTGCGGGCTCAACTCGCAGCCTGCACTTGAAACTATGTGTCTGGAG
    TTTGGGAGAGGCAAGTGGAATTCCAGGTGTAGCGGTGAAATGCGTAGATATCTGGAGGAAC
    ACCAGTGGCGAAGGCGACTTGCTGGCCTAAAACTGACGCTGAGGCACGAAAGCGTGGGTAG
    TGAACGGGATTAGATACCCCGGTAATCCACGCCCTAAACGTTGTCTACCAGTTGTTGGGGGG
    TTTTAACCCTCAGTAACGAACCTAACGGATTAAGTAGACCGCCTGGGGACTATGCTCGCAAG
    AGTGAAACTCAAAGGAATTGACGGGGGTCCGCACAAGCGGTGGAGCATGTGGTTTAATTCG
    ATGATACGCGAAAAACCTCACCTAGGCTTGACATGGAGTGGAATCATGTAGAGATACATGA
    GCCTTCGGGCCGCTTCACAGGTGCTGCATGGTTGTCGTCAGCTCGTGTCGTGAGATGTTGGG
    TTAAGTCCCGCAACGAGCGCAACCCTCACCTTATGTTGCCATCATTCAGTTGGGCACTCGTAA
    GGAACTGCCGGTGACAAACCGGAGGAAGGCGGGGATGACGTCAAATCCTCATGGCCTTTAT
    GTCTAGGGCAACACACGTGCTACAATGGCCGGTACAAAGGGTAGCCAACTCGCGAGGGGGA
    GCTAATCTCAAAAATCCGGTCCCAGTTCGGATTGGAGTCTGCAACTCGACTCCATGAAGTCG
    GAATCGCTAGTAATCGCGGATCAGCATGCCGCGGTGAATACGT-3'

12  5'-AACTAACGCTGGCGGCGCGTCTTAAACATGCAAGTCAAGCGGAGTAGCAATACTCA
    GCGGCGAACGGGTGAGTAACACGTGGGTAATCTTCCTCTGAGTCTGGGATAACTTTCCGA
    AAGGGAAGCTAATACTGGATGGTCCCGAGAGATCATAAGATTTTTCGGGTAAAGATTTATT
    GCTCGGAGATGAG-3'

13  5'-GTGTTCGGCCACAATGGAACTGAGACACGGTCCATACTCCTACGGGAGGCAGCAGTTA
    AGAATCTTGCTCAATGGGGGGAACCCTGAAGCAGCGACGCCGCGTGAACGATGAAGGTCT
    TCGGATTGTAAAGTTCAGTAAGCAGGGAAAAATAAGCAGCAATGTGATGATGGTACCTGC
    CTAAAGCACCGGCTAACTACGTGCCAGCAGCCGCGGTAATACGTATGGTGCAAGCGTTGTT
    CGGAATCATTGGGCGTAAAGGGTGCGTAGGCGGACATGTAAGTCAGGTGTGAAAACTGCG
    GGCTCAACTCGCAGCCTGCACTTGAAACTATGTGTCTGGAGTTTGGGAGAGGCAAGTGGAA
    TTCCAGGTGTAGCGGTGAAATGCGTAGATATCTGGAGGAACACCAGTGGCGAAGGCGACTT
    GCTGGCCTAAAACTGACGCTGAGGCACGAAAGCGTGGGTAGTGAACGGGATTAGATACCCC
    GGTAATCCACGCCCTAAACGTTGTCTACCAGTTGTTGGGGGTTTTAACCCTCAGTAACGAA
    CCTAACGGATTAAGTAGACCGCCTGGGGACTATGCTCGCAAGAGTGAAACTCAAAGGAATT
    GACGGGGGTCCGCACAAGCGGTGGAGCATGTGGTTTAATTCGATGATACGCGAAAAACCTC
    ACCTAGGCTTGACATGGAGTGGAATCATGTAGAGATACATGAGCCTTCGGGCCGCTTCACAG
    GTGCTGCATGGTTGTCGTCAGCTCGTGTCGTGAGATGTTGGGTTAAGTCCCGCAACGAGCGC
    AACCCTCACCTTATGTTGCCATCATTCAGTTGGGCACTCGTAAGGAACTGCCGGTGACAAAC
    CGGAGGAAGGCGGGGATGACGTCAAATCCTCATGGCCTTTATGTCTAGGGCAACACACGTG
    CTACAATGGCCGGTACAAAGGGTAGCCAACTCGCGAGGGGGAGCTAATCTCAAAAATCCGG
    TCCCAGTTCGGATTGGAGTCTGCAACTCGACTCCATGAAGTCGGAATCGCTAGTAATCGCGG
    ATCAGCATGCCGCGGTGAATACGT-3'

Additional primers that amplify a target nucleic acid sequence can be designed using, for example, a computer program such as OLIGO (Molecular Biology Insights, Inc., Cascade, CO). Important features when designing oligonucleotides to be used as amplification primers include, but are not limited to, an appropriate size amplification product to facilitate detection (e.g., by electrophoresis or real-time PCR), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 35 nucleotides in length.

In some embodiments, a mix of primers can be provided having degeneracy at one or more nucleotide positions. Degenerate primers are used in PCR where variability exists in the target sequence, i.e. the sequence information is ambiguous. Typically, degenerate primers will exhibit variability at no more than about 4, no more than about 3, preferably no more than about 2, and most preferably, no more than about 1 nucleotide position.

Designing oligonucleotides to be used as hybridization probes can be performed in a manner similar to the design of primers. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 60 nucleotides in length.

In a preferred embodiment, the *Leptospira* specific probe is 5' [6~FAM]-TGGGATAACTTTCCGAAAGGGAAGC-[BHQ1] 3' (SEQ ID NO: 3), although the skilled artisan will understand that other probes may be used. Alternative hybridization probes may be 70, 75, 80, 85, 90, 95, 96, 97, 98, or 99% identical to SEQ ID NO: 3. In other embodiments, probes may be designed such that they hybridize to and are suitable for detecting a target sequence of the *Leptospira* 16S gene. For instance, probes may be designed to hybridize to SEQ ID NO: 4, SEQ ID NO: 5, SEQ ID NO:

6, SEQ ID NO: 11, SEQ ID NO: 12, SEQ ID NO: 13, or fragments or complements thereof.

Probes may be between 10 and 30 nucleotides long. For instance, probes may be 10, 11, 12, 13, 14, 15, 16, 17, 18, 19, 20, 21, 22, 23, 24, 25, 26, 27, 28, 29, or 30 nucleotides in length. One of skill in the art will understand that the precise length and composition of a probe is dependent on the sample and the assay conditions. As disclosed herein, SEQ ID NO: 4, SEQ ID NO: 5, SEQ ID NO: 6, SEQ ID NO: 11, SEQ ID NO: 12, SEQ ID NO: 13, or fragments or complements thereof provide suitable target sequences for designing probes capable of detecting pathogenic *Leptospira*. In some embodiments a probe comprising 10-30 nucleotides of SEQ ID NO: 4, SEQ ID NO: 5, SEQ ID NO: 6, SEQ ID NO: 11, SEQ ID NO: 12, SEQ ID NO: 13, or fragments or complements thereof may be used for the detection of pathogenic *Leptospira*. In other embodiments, a probe that is at least 90%, at least 95%, or at least 99% identical to sequences comprising 10-30 nucleotides of SEQ ID NO: 4, SEQ ID NO: 5, SEQ ID NO: 6, SEQ ID NO: 11, SEQ ID NO: 12, SEQ ID NO: 13, or fragments or complements thereof may be used for the detection of pathogenic *Leptospira*. SEQ ID NO: 4, SEQ ID NO: 5, SEQ ID NO: 6, SEQ ID NO: 11, SEQ ID NO: 12, and SEQ ID NO: 13 are shown in Table 1 above.

Additional probes that can detect a target nucleic acid sequence can be designed using, for example, a computer program such as OLIGO (Molecular Biology Insights, Inc., Cascade, CO). Important features when designing oligonucleotides to be used as probes include, but are not limited to, an appropriate size target sequence to facilitate detection (e.g., by electrophoresis or real-time PCR), similar or higher melting temperatures compared to reaction primers (if being used in an amplification reaction like RT-PCR), and the length of the probe (i.e., the probe needs to be long enough to anneal with sequence-specificity but not so long that fidelity is reduced). Typically, oligonucleotide probes are 5 to 40 nucleotides in length.

Amplification and Detection of a Target Sequence:

Nucleic acid samples or isolated nucleic acids may be amplified by various methods known to the skilled artisan. Preferably, PCR is used to amplify nucleic acids of interest. Briefly, in PCR, two primer sequences are prepared that are complementary to regions on opposite complementary strands of a target sequence. An excess of deoxynucleotide triphosphates (dNTPs) are added to a reaction mixture along with a DNA polymerase, e.g., Taq polymerase.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. Cycling parameters can be varied, depending on the length of the amplification products to be extended. An internal positive amplification control (IPC) can be included in the sample, utilizing oligonucleotide primers and/or probes. The IPC can be used to monitor both the conversion process and any subsequent amplification.

In some embodiments, the PCR reaction may comprise thermocycling of 35, 40, 45, 46, 47, 48, 49, 50, 51, 52, 53, 54, 55, or up to 60 cycles. The denaturing temperature may range from about 95 to 105° C. or about 95° C., and the elongation temperature may range from about 50 to 75° C. or about 60° C. The cycling may be set up such that the denaturing temperature is maintained from 1 second to 3 minutes. The cycling may be set up such that the elongation temperature is maintained from 1 second to 3 minutes. One of skill in the art will know that these parameters may be optimized depending on, among other things, the samples and primers being used.

Real time PCR is performed using any suitable instrument capable of detecting the accumulation of the PCR amplification product. Most commonly, the instrument is capable of detecting fluorescence from one or more fluorescent labels. For example, real time detection on the instrument (e.g. an ABI Real-Time PCR System 7500® sequence detector) monitors fluorescence and calculates the measure of reporter signal, or Rn value, during each PCR cycle. The threshold cycle, or Ct value, is the cycle at which fluorescence intersects the threshold value. The threshold value can be determined by the sequence detection system software or manually.

Amplification of nucleic acids can be detected by any of a number of methods well-known in the art such as gel electrophoresis, column chromatography, hybridization with a probe, sequencing, melting curve analysis, or "real-time" detection. For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system, Scorpion™ primer system and use of intercalating dyes for double stranded nucleic acid.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Amplified nucleic acids for each of the target sequences may be detected simultaneously (i.e., in the same reaction vessel) or individually (i.e., in separate reaction vessels). For sequence-modified nucleic acids, the target may be independently selected from the top strand or the bottom strand. Thus, all targets to be detected may comprise top strand, bottom strand, or a combination of top strand and bottom strand targets.

In some embodiments, the *Leptospira* specific primers can be used in a polymerase chain reaction to amplify and detect pathogenic *Leptospira*. The PCR reaction may comprise sterile nuclease free water, forward and reverse primers, *Leptospira* specific probe(s), internal control primers, and a "master mix" comprising a DNA polymerase, dNTPs, salts, reaction buffer, and magnesium. Forward and reverse primers may be used at a reaction concentration ranging from 100 nM to 1.5 μM, or more particularly from 250-950 nM, 350-850 nM, 450-750 nM, 550-650 nM. In some embodiments, the forward and reverse primers may be used at a reaction concentration of 450, 460, 470, 480, 490, 500, 510, 520, 530, 540, 550, 560, 570, 580, 590, 600, 610, 620, 630, 640, 650, 670, 680, 690, 700, 710, 720, 730, 740, 750, 760, 770, 780, 790, 800, 810, 820, 830, 840, or 850 nM. *Leptospira* specific probes may be used at a reaction concentration ranging from 1-500 nM, or more particularly, from 25-400 nM, 50-300 nM, or 75-200 nM. In some embodiments, the *Leptospira* specific probe may be used at a reaction concentration of 50, 60, 70, 80, 90, 100, 110, 120, 130, 140, 150, 160, 170, 180, 190, 200, 210, 220, 230, 240, or 250 nM.

In some embodiments, the PCR master mix may contain a DNA polymerase, salts, magnesium, dNTPs, and reaction buffer, among other necessary and optional constituents.

TaqMan® probes (Heid, et al., Genome Res 6: 986-994, 1996) use the fluorogenic 5' exonuclease activity of Taq polymerase to measure the amount of target sequences in test samples. TaqMan® probes are oligonucleotides that contain a reporter dye usually at or near the 5' base, and a quenching moiety typically at or near the 3' base. The quencher moiety may be a dye, such as TAMRA, a Black Hole Quencher, or it may be a non-fluorescent molecule such as 4-(4-dimethylaminophenylazo) benzoic acid (DABCYL). See Tyagi, et al., 16 Nature Biotechnology 49-53 (1998). When irradiated, the excited fluorescent reporter transfers energy to the nearby quenching moiety by FRET rather than fluorescing. Thus, the close proximity of the reporter and quencher prevents emission of donor fluorescence while the probe is intact.

TaqMan® probes are designed to anneal to an internal region of a PCR product. When the polymerase replicates a template on which a TaqMan® probe is bound, its 5' exonuclease activity cleaves the probe. This ends the activity of the quencher (no FRET) and the reporter fluorophore starts to emit fluorescence which increases in each cycle proportional to the rate of probe cleavage. Accumulation of PCR product is detected by monitoring the increase in fluorescence of the reporter dye (note that primers may not be labeled). If the quencher is an acceptor fluorophore, then accumulation of PCR product can be detected by monitoring the decrease in fluorescence of the acceptor fluorophore.

Some embodiments of the disclosed compositions and methods comprise a probe specific for the *Leptospira* amplicon. The probe used for detection of the *Leptospira* amplicon may optionally be labeled with a reporter dye and a quencher as with a TaqMan® probe. For instance, an exemplary probe may comprise a FAM reporter dye on its 5' end and a BHQ-1 quencher on its 3' end. Those of skill in the art will know that this is only one example of numerous reporter day and quencher combinations that may be utilized in such an assay. Useful reporter dyes include, but are not limited to, BODIPY FL, FAM, 6-FAM, VIC, 4-acetamido-4'-isothiocyanatostilbene-2,2'disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamid, Oregon Green 488, Rhodamine green, Oregon Green 514, TET, Cal Gold, BODIPY R6G, Yakima Yellow, JOE, HEX, Cal Orange, BODIPY TMR-X, Quasar-570/Cy3, TAMRA, Rhodamine Red-X, Rhodamine Red, BODIPY 581/591, Cy3.5, ROX, Cal Red, Texas Red, BODIPY TR-X, BODIPY 630/665-X, Pulsar-650, Quasar-670/Cy5, and Cy5.5.

Suitable quenchers are selected based on the fluorescence spectrum of the particular fluorophore. Useful quenchers include, for example, the Black Hole™ quenchers BHQ-1, BHQ-2, and BHQ-3 (Biosearch Technologies, Inc.), and the ATTO-series of quenchers (ATTO 540Q, ATTO 580Q, and ATTO 612Q; Atto-Tec GmbH). Other useful quenchers include, but are not limited to, dabcyl, QSY 35, Eclipse, QSY 7, QSY 9, ElleQuencher, Iowa black, QSY 21, Qxl quenchers, Iowa black FQ, Iowa black RQ, and IRDye QC-1.

One of skill in the art will understand that certain pairing of reporter dyes and quenchers are preferred. For instance, in one embodiment, the reporter/quencher pair is 6-FAM/BHQ1. In another embodiment, the reporter may be Quasar-670, Cal Red, Quasar-570, or TAMRA and the quencher my BHQ-1, BHQ-2, or BHQ-3.

When the reporter dye and quencher are in close proximity (i.e. both are present on an intact oligonucleotide probe) the fluorescence of the reporter is suppressed. However, when the oligonucleotide probe is elongated in the disclosed assay, the 5'-3' nuclease activity of DNA polymerase will cleave the probe if it is bound specifically to the target sequence between the forward and reverse primer sites. This releases the reporter dye and quencher, and upon excitation, the fluorescent signal produced by the reporter dye is no longer quenched. This results in an increase in fluorescence that can be detected.

In some embodiments of the disclosed compositions and methods, Black Hole Quencher may be used to reduce background. In a preferred embodiment, the *Letospira* specific probe comprises a reporter dye and a quencher so that it can be detected upon amplification of the target sequence.

Additional, detectable labels include, but are not limited to, radioisotopes (e.g., $^{32}P$, $^{35}S$, $^{3}H$, $^{14}C$, $^{125}I$, $^{131}I$), electron-dense reagents (e.g., gold), enzymes (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively.

The label can be directly incorporated into the nucleic acid to be detected, or it can be attached to a probe (e.g., an oligonucleotide) or antibody that hybridizes or binds to the nucleic acid to be detected. A label can be attached either directly or indirectly to probes or primers, and a label may be attached by covalent or non-covalent means. A label can be attached by spacer arms of various lengths to reduce potential steric hindrance or impact on other useful or desired properties. See, e.g., Mansfield, 9 *Mol. Cell*. Probes 145-156 (1995). Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, and then incorporated into nucleic acids during nucleic acid synthesis or amplification.

Alternatively, the detectable labels may be part of a Scorpion detection system. With Scorpion detection systems, sequence-specific priming and PCR product detection is achieved using a single molecule. The Scorpion probe maintains a stem-loop configuration in the unhybridized state. The fluorophore is quenched by a moiety coupled to the 5' end, although in suitable embodiments, the fluorophore is attached to the 5' end and is quenched by a moiety coupled to the 3' end. The 3' portion of the stem also contains a sequence that is complementary to the extension product of the primer. This sequence is linked to the 5' end of the Scorpion probe via a non-amplifiable monomer. After extension using the Scorpion primer, the specific probe sequence is able to bind to its complement within the extended amplicon thus opening up the hairpin loop. This prevents fluorescence from being quenched and a signal is observed. A specific target is amplified by the reverse primer and the primer portion of the Scorpion, resulting in an extension product. A fluorescent signal is generated due to the separation of the fluorophore from the quencher resulting from the binding of the probe element of the Scorpion to the extension product.

Internal Controls:

To ensure the absence of non-specific PCR inhibitors in a sample, an internal positive amplification control (IPC) may be included with each specimen. The positive control primers and probe can be added to create a multiplex reaction with the target and sample primers. The IPC amplicon can be detected with a probe labeled with a reporter dye attached to the 5' end of the probe. A sample can be interpreted as negative if the analysis of the internal positive control indicates that DNA amplification has occurred in the reaction tube but there was no detection of the *Leptospira* specific probe.

EXAMPLES

Example 1. Sample Preparation and DNA Extraction

One 250 µl aliquot of "*Leptospira* Positive Control" control was removed and thawed at room temperature. 200 µl sterile water was used for a negative control. 1 positive and 1 negative control were performed for each batch of extractions. 200 µl of control or specimen was pipetted into a given well of the sample cartridge. Refrigerated or frozen urine samples mixed with urine transport media were allowed to warm to room temperature (18° to 26° C.) before loading into the sample cartridge.

Internal Positive Control DNA was added to a lysis buffer prior to extraction, and 200 µl was added to each well containing a sample.

Example 2. DNA Amplification and Detection

DNA amplification was carried out using an ABI 7500 Real-Time PCR System. Prior to amplification, samples were combined with a master mix.

The amplification plots of the controls were examined. The plots showed a sigmoidal curve with a distinct exponential growth phase followed by a plateau phase.

Sample amplifications were examined as well. Negative plots were only visible as a line near the bottom of the graph, due to poor resolution at lower fluorescence values.

Figure 1B:
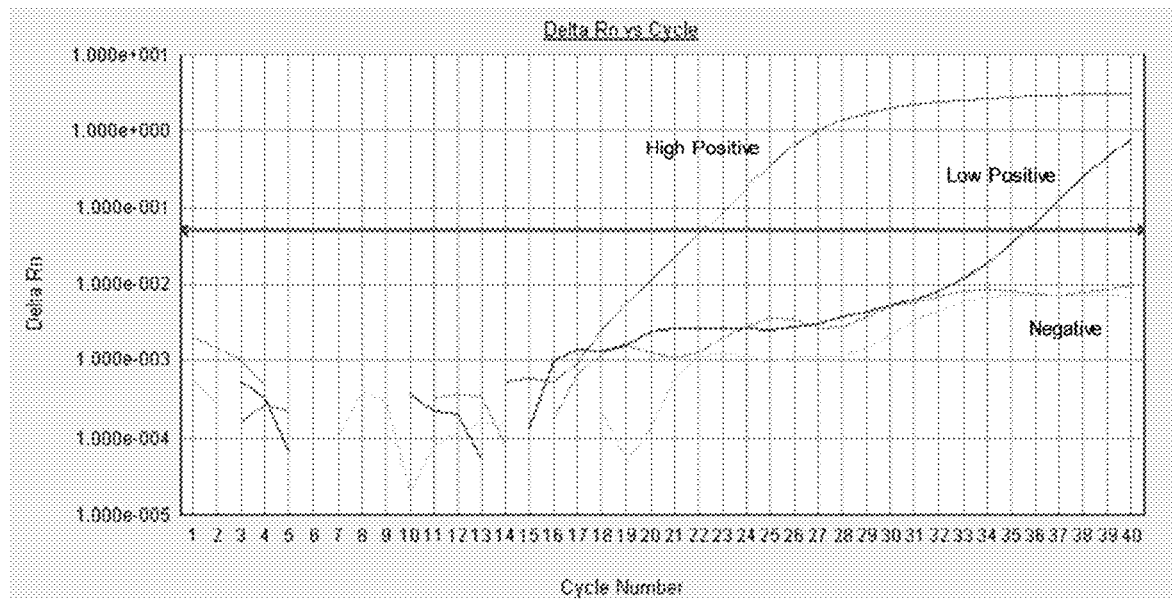

An example of typical curves for the *Leptospira* assay are shown in FIGS. 1A and 1B. The curve on the left is typical of a high positive result. The curve on the right is typical of a low positive result. The horizontal line is the threshold. All positive results cross this line. The cycle at which a given plot crosses the threshold line is called the Threshold Cycle (Ct). Negative plots do not have sigmoidal shape, and/or do not cross the threshold line. The data may be viewed in a linear format, as in FIG. 1A, or a log format, as in FIG. 1B. The decision on which format to use to visualize amplification plots is left to the discretion of the technician, however each plot has advantages. Positive results may be more intuitively obvious in linear format, since only positive plots are distinguishable above the background in this format. Log view, however, allows better discernment of small differences between plot lines, especially at low fluorescence.

If the amplification plots of the controls do not show curves, it may be an indication that there has been contamination, improper preparation of the master mix or the controls, or degradation of the fluorescent probe. The IPC must amplify, and it must be within the specified Ct range for the IPC result to be valid. If the IPC results are out of the specified Ct range and targets are not detected, then target results may not be valid.

Examination of clinical samples was done after the controls were examined and shown to have the correct results. Amplification plots were examined for every sample. When the amplification plot showed an exponential increase the amplification curve was considered a valid, positive result.

Example 3: Validation of Primers and Probes for Distinguishing Pathogenic and Non-Pathogenic *Leptospira*

*Leptospira weillii* (ATCC #43285) is a non-interrogans pathogen which might have trouble being detected in the *Leptospira* assay. Multiple sets of primers were tested in order to determine effectiveness of detection.

For validation, thawed bacteria from ATCC was diluted 10 times and frozen in 250 µl or 1 ml aliquots. Thawed samples were extracted for DNA. Samples were roughly estimated to have $10^8$ cells/ml. DNA from serial dilutions of the bacteria were used to determine the detection limits of various primer pairs.

Three different sets of primer pairs were used for validation tests. Set 1 consisted of primers F76 and R148, Set 2 consisted of F71 and R148, and Set 3 consisted of FSmythe and RSmythe. The sequences of these primers can be found in Table 2. For Sets 1 and 2, probe P101 was used to detect target sequence amplification, and for Set 3, PSmythe was used to detect target sequence amplification.

TABLE 2

Sequences of Primers and Probes

| Name | Sequence | SEQ ID NO: |
|---|---|---|
| F76 | 5'-CACGTGGGTAATCTTCCTCTG-3' | 7 |
| R148 | 5'-TCTCTCGGGACCATCCAGTA-3' | 2 |
| F71 | 5'-AGTAACACGTGGGTAATCTTCCT-3' | 1 |
| FSmythe | 5'-CCCGCGTCCGATTAG-3' | 8 |
| RSmythe | 5'-TCCATTGTGGCCGR*ACAC-3' | 9 |
| P101 | 5'-TGGGATAACTTTCCGAAAGGGAAGC-3' | 3 |
| PSmythe | 5'-CTCACCAAGGCGACGATCGGTAGC-3' | 10 |

*R indicates a position that is A 50% of the time and G 50% of the time. Primer lots meeting this condition can be bought commercially.

100 µM of each primer in a given set and 10 µM of the corresponding probe were combined in a reaction mixture comprising master mix, taq polymerase, *Leptospira weillii* DNA, and water. Thermocycling was carried out using an ABI 7500 Real-Time PCR System The results of the real time detection of amplification are found in Table 3.

TABLE 3

Detection Results of Primer Sets

| Cell/ml | Replicate 1 | Replicate 2 | Replicate 3 | Average Ct | St. Dev. | % CV |
|---|---|---|---|---|---|---|
| | | Primer Set 1 | | | | |
| $10^8$ | 22.68 | 23.68 | 22.38 | 22.91 | 0.681 | 2.97 |
| $10^7$ | 26 | 25.99 | 25.69 | 25.89 | 0.176 | 0.68 |
| $10^6$ | 29.82 | 28.62 | 29.35 | 29.26 | 0.605 | 2.07 |

TABLE 3-continued

Detection Results of Primer Sets

| Cell/ml | Replicate 1 | Replicate 2 | Replicate 3 | Average Ct | St. Dev. | % CV |
|---|---|---|---|---|---|---|
| $10^5$ | 33.95 | 31.77 | 33.28 | 33 | 1.117 | 3038 |
| $10^4$ | 37.63 | 34.6 | 37.35 | 36.53 | 1.674 | 4.58 |
| Negative | 45.92 | Undetected | 43.2 | — | — | — |
| Primer Set 2 | | | | | | |
| $10^8$ | 21.64 | 22.39 | 21.47 | 21.83 | 0.49 | 2.24 |
| $10^7$ | 24.89 | 25.07 | 24.5 | 24.82 | 0.291 | 1.17 |
| $10^6$ | 28.53 | 28.39 | 34.07 | 30.33 | 3.24 | 10.68 |
| $10^5$ | 32.2 | 30.64 | 31.77 | 31.54 | 0.806 | 2.55 |
| $10^4$ | 35.79 | 34.71 | 35.52 | 35.34 | 0.562 | 1.59 |
| Negative | Undetected | Undetected | Undetected | — | — | — |
| Primer Set 3 | | | | | | |
| $10^8$ | 18.08 | 17.96 | 17.97 | 18 | 0.067 | 0.37 |
| $10^7$ | 21.18 | 21.29 | 21.28 | 21.25 | 0.061 | 0.29 |
| $10^6$ | 25.06 | 24.86 | 25.07 | 25 | 0.118 | 0.47 |
| $10^5$ | 28.9 | 29.12 | 28.79 | 28.94 | 0.168 | 0.58 |
| $10^4$ | 33.57 | 32.7 | 33.27 | 33.18 | 0.442 | 1.33 |
| Negative | Undetected | Undetected | Undetected | — | — | — |

Figure 2A:
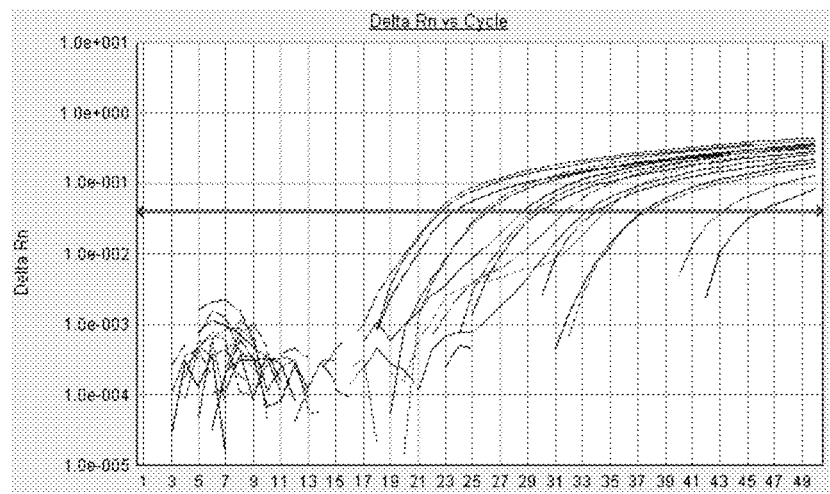
FIGS. 2A-2C show the results from the validation of primer and probe sets. Set 1 is shown in FIG. 2A, Set 2 is shown in FIG. 2B, and Set 3 is shown in FIG. 2C.
Figure 2B:
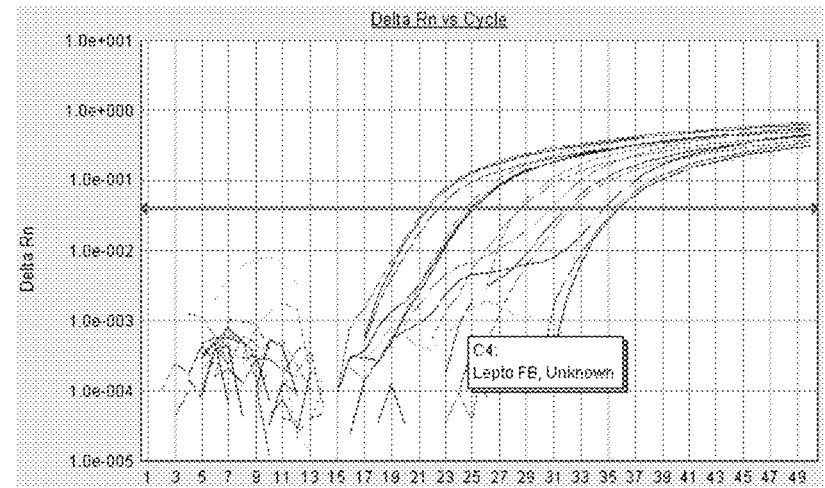
Figure 2C:
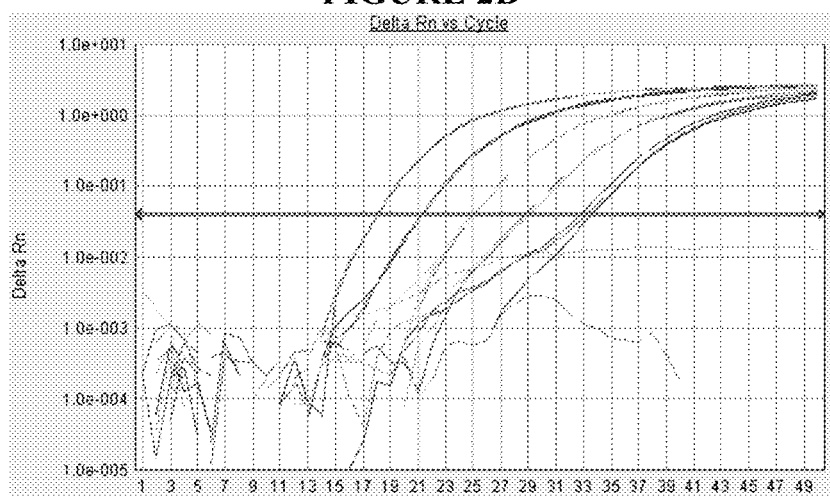

The cycling output data can be seen in FIG. 2. The bold horizontal lines represent the threshold limit.

The PCR efficiency of Set 1 was 97.8%. The PCR efficiency of Set 2 was 99.0%. The PCR efficiency of Set 3 was 91.3%. While the primer sets differed in terms of Ct scores, Sets 1 and 2 had significantly higher PCR efficiencies than Set 3. This validation indicates that Sets 1 and 2 are more suitable for reliable detection of pathogenic *Leptospira*. Additionally, Sets 1 and 2 had superior limits of detection than Set 3, indicating that Set 3 would likely have trouble detecting some species of *Leptospira*.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Non-limiting embodiments are set forth within the following claims.

What is claimed is:

1. A kit comprising a set of substantially purified oligonucleotides comprising oligonucleotides having the sequences consisting of:

(i)
(SEQ ID NO: 1)
5'- AGTAACACGTGGGTAATCTTCCT -3', (ii)
(SEQ ID NO: 2)
5'- TCTCTCGGGACCATCCAGTA -3',
and (iii)
(SEQ ID NO: 3)
5'- TGGGATAACTTTCCGAAAGGGAAGC -3', wherein said oligonucleotide of (iii) is attached either directly or indirectly to a detectable label, wherein the detectable label comprises a reporter dye and a quencher.

2. The kit of claim 1, wherein the oligonucleotide of (iii) is 5'[6~FAM]-TGGGATAACTTTCCGAAAGGGAAGC-[BHQ-1]3' (SEQ ID NO: 3).

3. A composition comprising:

a pair of substantially pure oligonucleotide primers consisting of SEQ ID NO: 1 and SEQ ID NO: 2, and a detectably labelled probe consisting of the sequence of SEQ ID NO: 3, wherein the detectable label comprises a reporter dye and a quencher.

4. The composition of claim 3, wherein the reporter dye is 6~FAM.

5. The composition of claim 3, wherein the quencher is BHQ-1.

* * * * *

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agtaacacgt gggtaatctt cct                                              23

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctctcggga ccatccagta                                                  20
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' Optional 6-FAM
<220> FEATURE:
<223> OTHER INFORMATION: 3' Optional BHQ-1

<400> SEQUENCE: 3
tgggataact tccgaaagg gaagc                                          25

<210> SEQ ID NO 4
<211> LENGTH: 1321
<212> TYPE: DNA
<213> ORGANISM: Leptospira sp.

<400> SEQUENCE: 4
aactaacgct ggcggcgcgt cttaaacatg caagtcaagc ggagtagcaa tactcagcgg    60
cgaacgggtg agtaacacgt gggtaatctt cctccgagtc tgggataact tccgaaagg   120 ggagctaata ctggatggtc ccgagagagg tcatatgatt tttcgggtaa agatttattg   180
ctcggagctg agcccgcgcc cgattagcta gttggtgagg taatggctca ccaaggcgac   240
gatcggtagc cggcctgaga gggtgttcgg ccacaatgga actgagacac ggtccatact   300
cctacgggag gcagcagtta agaatcttgc tcaatggggg gaaccctgaa gcagcgacgc   360
cgcgtgaacg atgaaggtct cggattgta aagttcaata agcaggaaaa ataagcagc    420 gatgtgatga tggtacctgc ctaaagcacc ggctaactac gtgccagcag ccgcggtaat   480
acgtatggtg caagcgttgt tcggaatcat tgggcgtaaa gggtgcgtag gcggacatgt   540
aagtcaggtg tgaaaactgc gggctcaact cgcagcctgc acttgaaact atgtgtctgg   600
agtttgggag aggcaagtgg aattccaggt gtagcggtga aatgcgtaga tatctggagg   660
aacaccagtg gcgaaggcga cttgctggcc taaaactgac gctgaggcac gaaagcgtgg   720
gtagtgaacg ggattagata ccccggtaat ccacgcccta acgttgtct accagttgtt   780 gggggtttta accctcagta acgaacctaa cggattaagt agaccgcctg ggactatgc   840 tcgcaagagt gaaactcaaa ggaattgacg ggggtccgca caagcggtgg agcatgtggt   900
ttaattcgat gatacgcgaa aaacctcacc taggcttgac atggagtgga attatgtaga   960
gatacatgag ccttcgggcc gcttcacagg tgctgcatgg ttgtcgtcag ctcgtgtcgt  1020
gagatgttgg gttaagtccc gcaacgagcg caaccctcac cttatgttgc catcatttag  1080
ttgggcactc gtaaggaact gccggtgaca aaccggagga aggcgggat gacgtcaaat   1140 cctcatggcc tttatgtcta gggcaacaca cgtgctacaa tggccggtac aaagggtagc  1200
caactcgcga gggggagcta atctcaaaaa gccggtccca gttcggattg gagtctgcaa  1260
ctcgactcca tgaagtcgga atcgctagta atcgcggatc agcatgccgc ggtgaatacg  1320
t                                                                  1321

<210> SEQ ID NO 5
<211> LENGTH: 192
<212> TYPE: DNA
<213> ORGANISM: Leptospira sp.

<400> SEQUENCE: 5

```
aactaacgct ggcggcgcgt cttaaacatg caagtcaagc ggagtagcaa tactcagcgg    60
cgaacgggtg agtaacacgt gggtaatctt cctccgagtc tgggataact ttccgaaagg   120
ggagctaata ctggatggtc ccgagagagg tcatatgatt tttcgggtaa agatttattg   180
ctcggagctg ag                                                       192

<210> SEQ ID NO 6
<211> LENGTH: 1059
<212> TYPE: DNA
<213> ORGANISM: Leptospira sp.

<400> SEQUENCE: 6
gtgttcggcc acaatggaac tgagacacgg tccatactcc tacgggaggc agcagttaag    60
aatcttgctc aatgggggga accctgaagc agcgacgccg cgtgaacgat gaaggtcttc   120
ggattgtaaa gttcaataag cagggaaaaa taagcagcga tgtgatgatg gtacctgcct   180
aaagcaccgg ctaactacgt gccagcagcc gcggtaatac gtatggtgca agcgttgttc   240
ggaatcattg ggcgtaaagg gtgcgtaggc ggacatgtaa gtcaggtgtg aaaactgcgg   300
gctcaactcg cagcctgcac ttgaaactat gtgtctggag tttgggagag caagtggaa   360 ttccaggtgt agcggtgaaa tgcgtagata tctggaggaa caccagtggc gaaggcgact   420
tgctggccta aaactgacgc tgaggcacga aagcgtgggt agtgaacggg attagatacc   480
ccggtaatcc acgccctaaa cgttgtctac cagttgttgg gggttttaac cctcagtaac   540
gaacctaacg gattaagtag accgcctggg gactatgctc gcaagagtga aactcaaagg   600
aattgacggg ggtccgcaca agcggtggag catgtggttt aattcgatga tacgcgaaaa   660
acctcaccta ggcttgacat ggagtggaat tatgtagaga tacatgagcc ttcgggccgc   720
ttcacaggtg ctgcatggtt gtcgtcagct cgtgtcgtga gatgttgggt taagtcccgc   780
aacgagcgca accctcacct tatgttgcca tcatttagtt gggcactcgt aaggaactgc   840
cggtgacaaa ccggaggaag gcggggatga cgtcaaatcc tcatggcctt tatgtctagg   900
gcaacacacg tgctacaatg gccggtacaa agggtagcca actcgcgagg gggagctaat   960
ctcaaaaagc cggtcccagt tcggattgga gtctgcaact cgactccatg aagtcggaat  1020
cgctagtaat cgcggatcag catgccgcgg tgaatacgt                         1059

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cacgtgggta atcttcctct g                                             21

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccgcgtccg attag                                                    15
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 9
tccattgtgg ccgracac                                                      18

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 10
ctcaccaagg cgacgatcgg tagc                                               24

<210> SEQ ID NO 11
<211> LENGTH: 1320
<212> TYPE: DNA
<213> ORGANISM: Leptospira sp.

<400> SEQUENCE: 11
aactaacgct ggcggcgcgt cttaaacatg caagtcaagc ggagtagcaa tactcagcgg         60
cgaacgggtg agtaacacgt gggtaatctt cctctgagtc tgggataact ttccgaaagg        120
gaagctaata ctggatggtc ccgagagatc ataagatttt tcgggtaaag atttattgct        180
cggagatgag cccgcgtccg attagctagt tggtgaggta aaggctcacc aaggcgacga        240
tcggtagccg gcctgagagg gtgttcggcc acaatggaac tgagacacgg tccatactcc        300
tacgggaggc agcagttaag aatcttgctc aatgggggga accctgaagc agcgacgccg        360
cgtgaacgat gaaggtcttc ggattgtaaa gttcagtaag cagggaaaaa taagcagcaa        420
tgtgatgatg gtacctgcct aaagcaccgg ctaactacgt gccagcagcc gcggtaatac        480
gtatggtgca agcgttgttc ggaatcattg ggcgtaaagg gtgcgtaggc ggacatgtaa        540
gtcaggtgtg aaaactgcgg gctcaactcg cagcctgcac ttgaaactat gtgtctggag        600
tttgggagag gcaagtggaa ttccaggtgt agcggtgaaa tgcgtagata tctggaggaa        660
caccagtggc gaaggcgact tgctggccta aaactgacgc tgaggcacga aagcgtgggt        720
agtgaacggg attagatacc ccggtaatcc acgccctaaa cgttgtctac cagttgttgg        780
ggggttttaa ccctcagtaa cgaacctaac ggattaagta gaccgcctgg ggactatgct        840
cgcaagagtg aaactcaaag gaattgacgg gggtccgcac aagcggtgga gcatgtggtt        900
taattcgatg atacgcgaaa aaccctcacct aggcttgaca tggagtggaa tcatgtagag        960
atacatgagc cttcgggccg cttcacaggt gctgcatggt tgtcgtcagc tcgtgtcgtg       1020
agatgttggg ttaagtcccg caacgagcgc aaccctcacc ttatgttgcc atcattcagt       1080
tgggcactcg taaggaactg ccggtgacaa accggaggaa ggcggggatg acgtcaaatc       1140
ctcatggcct ttatgtctag gcaacacacg tgctacaat ggccggtaca aagggtagcc       1200
aactcgcgag ggggagctaa tctcaaaaat ccggtcccag ttcggattgg agtctgcaac       1260
tcgactccat gaagtcggaa tcgctagtaa tcgcggatca gcatgccgcg gtgaatacgt       1320

```
<210> SEQ ID NO 12
<211> LENGTH: 190
<212> TYPE: DNA
<213> ORGANISM: Leptospira sp.

<400> SEQUENCE: 12
aactaacgct ggcggcgcgt cttaaacatg caagtcaagc ggagtagcaa tactcagcgg    60
cgaacgggtg agtaacacgt gggtaatctt cctctgagtc tgggataact ttccgaaagg   120
gaagctaata ctggatggtc ccgagagatc ataagatttt tcgggtaaag atttattgct   180
cggagatgag                                                          190

<210> SEQ ID NO 13
<211> LENGTH: 1060
<212> TYPE: DNA
<213> ORGANISM: Leptospira sp.

<400> SEQUENCE: 13
gtgttcggcc acaatggaac tgagacacgg tccatactcc tacgggaggc agcagttaag    60
aatcttgctc aatgggggga accctgaagc agcgacgccg cgtgaacgat gaaggtcttc   120
ggattgtaaa gttcagtaag cagggaaaaa taagcagcaa tgtgatgatg gtacctgcct   180
aaagcaccgg ctaactacgt gccagcagcc gcggtaatac gtatggtgca agcgttgttc   240
ggaatcattg ggcgtaaagg gtgcgtaggc ggacatgtaa gtcaggtgtg aaaactgcgg   300
gctcaactcg cagcctgcac ttgaaactat gtgtctggag tttgggagag gcaagtggaa   360
ttccaggtgt agcggtgaaa tgcgtagata tctggaggaa caccagtggc gaaggcgact   420
tgctggccta aaactgacgc tgaggcacga aagcgtgggt agtgaacggg attagatacc   480
ccggtaatcc acgccctaaa cgttgtctac cagttgttgg ggggttttaa ccctcagtaa   540
cgaacctaac ggattaagta gaccgcctgg ggactatgct cgcaagagtg aaactcaaag   600
gaattgacgg gggtccgcac aagcggtgga gcatgtggtt taattcgatg atacgcgaaa   660
aacctcacct aggcttgaca tggagtggaa tcatgtagag atacatgagc cttcgggccg   720
cttcacaggt gctgcatggt tgtcgtcagc tcgtgtcgtg agatgttggg ttaagtcccg   780
caacgagcgc aaccctcacc ttatgttgcc atcattcagt tgggcactcg taaggaactg   840
ccggtgacaa accggaggaa ggcggggatg acgtcaaatc ctcatggcct ttatgtctag   900
ggcaacacac gtgctacaat ggccggtaca aagggtagcc aactcgcgag ggggagctaa   960
tctcaaaaat ccggtcccag ttcggattgg agtctgcaac tcgactccat gaagtcggaa  1020
tcgctagtaa tcgcggatca gcatgccgcg gtgaatacgt                        1060
```